United States Patent [19]

Hoebel et al.

[11] Patent Number: 5,400,792
[45] Date of Patent: Mar. 28, 1995

[54] MEDICAL DIAGNOSTICS INSTALLATION CONTROLLABLE FROM A CENTRAL WORK STATION

[75] Inventors: Peter Hoebel, Buckenhof; Thomas Engel, Erlangen; Juergen Ussmueller, Stegaurach; Kurt Schwarzmann, Hoechstadt, all of Germany

[73] Assignee: Siemens Aktiengesellschaft, Munich, Germany

[21] Appl. No.: 274,583

[22] Filed: Jul. 13, 1994

Related U.S. Application Data

[63] Continuation of Ser. No. 48,070, Apr. 13, 1993, abandoned, which is a continuation-in-part of Ser. No. 773,537, Oct. 9, 1991, abandoned.

[30] Foreign Application Priority Data

Nov. 20, 1990 [EP] European Pat. Off. ............ 90122194

[51] Int. Cl.[6] .............................................. A61B 5/0205
[52] U.S. Cl. .................................. 128/670; 364/413.13
[58] Field of Search ............................... 128/670–671, 128/903, 906; 364/413.01–413.04, 413.13

[56] References Cited

U.S. PATENT DOCUMENTS

| 3,675,640 | 7/1972 | Gatts | 128/671 |
| 4,483,342 | 11/1984 | Pfeifer | 128/653 |
| 4,688,577 | 9/1987 | Bro | 128/670 |
| 4,803,625 | 2/1989 | Fu et al. | 128/906 |
| 4,838,275 | 6/1989 | Lee | 128/670 |
| 5,002,055 | 3/1991 | Merki et al. | 128/635 |
| 5,050,613 | 9/1991 | Newman et al. | 128/670 |

FOREIGN PATENT DOCUMENTS

| 2178596 | 11/1973 | France . |
| 2594321 | 4/1987 | France . |
| 2641180 | 7/1990 | France . |

Primary Examiner—Angela D. Sykes
Attorney, Agent, or Firm—Hill, Steadman & Simpson

[57] ABSTRACT

A medical diagnostics installation, such as an x-ray angiography installation, has a number of separate treatment and data-acquisition components, all of which are connected to a central work station having an operating area accessible by a single user for central operation and monitoring of all components. Data acquisition, storage and distribution of the patient data take place at the work station using monitors. Data flow, for example parameters for obtaining an optimum image quality, can thereby be coordinated at one location.

1 Claim, 2 Drawing Sheets

MEDICAL DIAGNOSTICS INSTALLATION CONTROLLABLE FROM A CENTRAL WORK STATION

This is a continuation of application Ser. No. 08/048,070, filed Apr. 13, 1993, now abandoned, which is a continuation-in-part of application Ser. No. 07/773,537, filed Oct. 9, 1991, now abandoned.

BACKGROUND OF THE INVENTION

1. Field of the Invention

The present invention is directed to a medical diagnostics installation of the type such as an x-ray angiography system having a number of separate treatment and data-acquisition components.

2. Description of the Prior Art

Medical diagnostics installations, such as x-ray angiography systems, are known which include a number of separate components for facilitating treatment of, or acquiring data from, a patient. X-ray angiography systems, for example, include an x-ray generator, means for acquiring x-ray images, a contrast agent injector, and one or more patient monitoring units, such as an ECG unit. Very high image quality demands are made in a medical diagnostics installation of this type.

There is a need for an optimally simple and easily surveyable operation of such installations, so that the examining personnel can fully concentrate on the patient. In known systems, the multitude of control panels makes manipulation of the installation, for example to obtain the optimum image quality, more difficult, and may be the cause of errors.

SUMMARY OF THE INVENTION

It is an object of the present invention to provide a medical diagnostics installation of the type having a plurality of components which interact with an examination subject which provides simplified operation and patient monitoring, particularly in the acquisition of patient data and treatment parameters.

The above object is achieved in accordance with the principles of the present invention in a medical diagnostics installation having a plurality of patient-interactive components which are which are all connected to a central work station from which the components can be operated and monitored. Data are acquired by certain of the components, for example an ECG unit, and the data are reproduced either synchronously or chronologically at the work station. The work station is constructed for displaying, acquiring and setting the operating parameters of the components. Using this central work station, the operation and monitoring of the components as well as the acquisition of patient data, takes place centrally at a uniform operating area. Consequently, the control elements for the individual components are not located at the respective components themselves, but are incorporated in a complete system operable from one location. It is possible to coordinate and program the operation being undertaken at the installation with the interaction of most or all of the components being computer-controlled.

This type of installation is particularly suitable for x-ray angiography, i.e., for installations examining the blood vessels of a patient, particularly the cardiac blood vessels. The system disclosed herein can be used, however, in any installation for administering treatment to a patient. As used herein, the term "treatment" is not strictly limited to therapy-administering procedures, but also encompasses examination procedures.

DESCRIPTION OF THE PREFERRED EMBODIMENTS

Figure 1:
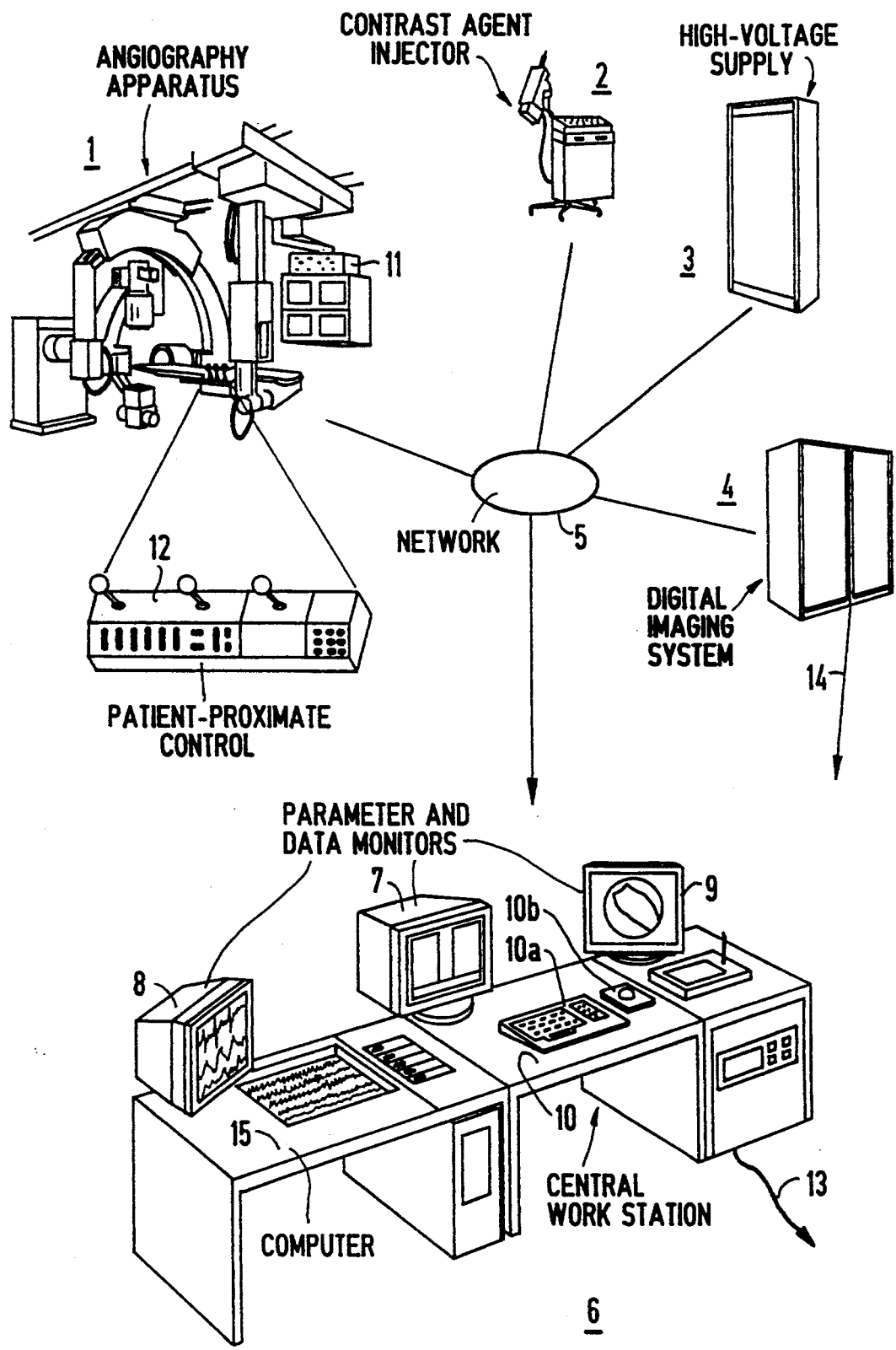
FIG. 1 illustrates a medical diagnostics installation constructed in accordance with the principles of the present invention having a plurality of components shown schematically interrelated and connected to a central work station.

A medical diagnostics installation, in the exemplary embodiment of a bi-planar x-ray angiography system for cardiac examination, is shown in FIG. 1. The image generating system is generally referenced 1, by which a patient can be transilluminated with x-rays in the cardiac region from two perpendicular directions. For portraying the blood vessels of the patient, the patient is injected with a contrast agent, using a contrast agent injector 2. Generation of the x-rays for creating the image is undertaken with an x-ray tube, contained within the system 1, which is fed by a high-voltage supply 3. Setting the operating parameters of the high-voltage supply 3, in turn, determines the operating parameters for the x-ray tube, including a dose rate. A digital imaging system 4 is provided for the digital acquisition, processing and storing of the x-ray images which are generated.

The components 1 through 4 are interconnected via a network 5 through which data are transmitted.

The network 5 is connected to a central work station 6 having monitors 7, 8 and 9, and an operating area 10. The central work station 6 controls and monitors the components 1 through 4 (and such other components as may be present), and also serves for the acquisition of patient information.

The operating parameters of the components 1 through 4 are set at the central work station 6 using the controls at the operating area 10, coordinated with the displays on the respective monitors 7, 8 and 9. The patient support may, for example, be displaced via the central work station 6 for optimum positioning of the patient within the angiography installation 1, the parameters of the x-ray tubes of the two x-ray systems of the angiography installation I can be set (such as filament current, anode voltage, and exposure time), as can the parameters of the contrast injector 2. The values which are set in this manner are displayed on the monitors 7, 8 and 9 and can be surveyed from a single location.

Additionally, one or more of the monitors, such as the monitor 8, may be used to display measured physiological values of the patient. For example, the measured values supplied by an EKG unit 11 may be transmitted to the work station 6 via the network 5 synchronized with the image information, all of which can be displayed on the monitor 8.

The central work station 6 may be used not only for controlling and monitoring the components 1 through 4 during normal operation, but can also be used for service purposes. A service technician, for example, can set specific parameters for service purposes from the work station 6, and can monitor such settings.

For the direct operation of the components, operating elements for this purpose can be optionally arranged at a location proximate to the patient. For example, a control panel 12 can be placed at the angiography installation. Whereas the operation of the installation proceeding from the control panel 12 ensues via switches, levers and the like, operation at the work station 6 ensues at the operating area 10 using a keyboard connected to a central computer 15 disposed at the work station 6. The computer 15 is connected to the network 5, and can be connected via a line 13 to a clinical computer for data exchange. The digital imaging system 4 may be connected via a line 14 to a central image-archiving system.

In the exemplary angiography system, the plurality of operating elements are integrated at the work station 6, namely at the operating area thereof, such as in the form of an optical pointer operation, for example a keyboard 10a or a mouse 10b. The keyboard 10a controls the computer 15. Operation of the components 1 through 4 proceeds therefrom. The monitoring of these components and the acquisition of physiological data also takes place centrally using the monitors 7, 8 and 9. A large number of separate operating locations as is required in conventional systems, is consequently avoided in the installation in accordance with the principles of the present invention.

Accordingly, pursuant to the present invention, one can employ a central work station 6, located at one location, to operate a plurality of different medical examination systems. Each of those medical examination systems includes a plurality of system components. Some of those system components are components which have operating parameters associated therewith, and some of those system components are components for acquiring data from a patient. All of these various system components are controllable at the central work station 6, thereby providing centralized control of all of the systems at one location, possibly by one person.

Heretofore, each medical examination system has had its own work station, dedicated exclusively for operating that system. Yet, this constitutes a hinderance, for example, in an operating room environment, wherein a number of such medical examination systems may be employed simultaneously, or in sequence. The necessity of providing a separate work station for each medical examination apparatus has heretofore not only required increased space in an already-crowded environment, but also has required either one operator to physically move from work station to work station, or has required a number of different operators respectively situated at each different work station.

FIG. 1 shows but one embodiment for implementing the foregoing. One of ordinary skill in the relevant art can easily construct the embodiment shown in the figure, or different variations thereof based on the description herein.

The hardware for accomplishing the interconnection of the system of FIG. 1 is well within the knowledge of those of ordinary skill in the art, and except for certain programming details, which would also be well within the skill of a routineer programmer, the hardware interface and software driver elements are well-known to those skilled in the art. Many of the same components which have been used in the past to connect a particular medical examination apparatus to its dedicated work station can be used, with minor modification (if any), to connect that same system to the central work station 6.

Figure 2:
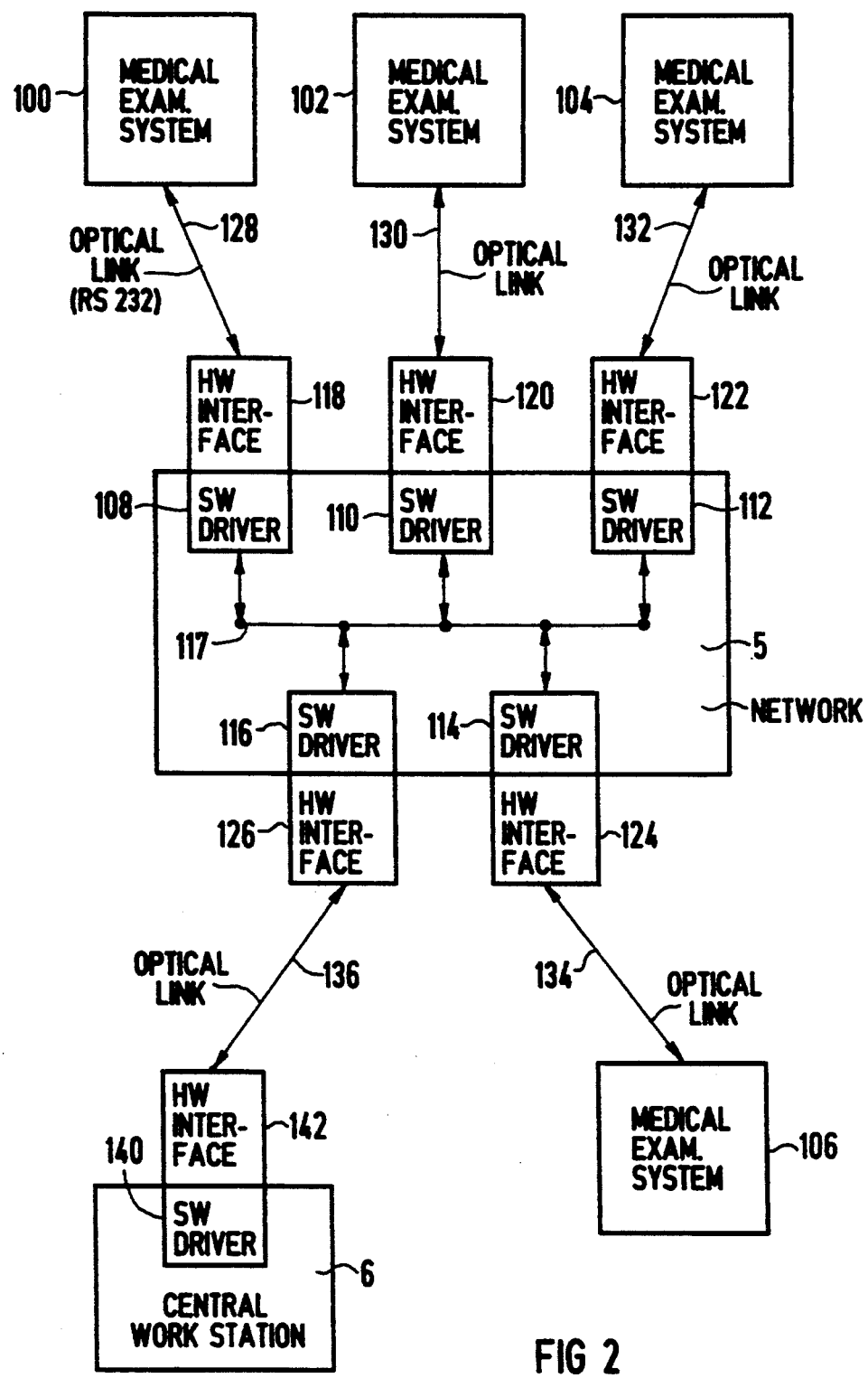
FIG. 2 illustrates a block diagram of a network for use in a medical diagnostics installation.

However, a more detailed example is illustrated in FIG. 2, all of which would be within the skill of a person knowledgeable in this art, of the concept of controlling different medical examination systems 100, 102, 104 and 106 from a central work station 6 disposed at one location of the network 5. As shown in FIG. 2, the network 5 can include a software driver 108, 110, 112, 114 or 116, respectively, for each system and the central work station with which it is intended to interact, all of the software drivers being connected by a bi-directional data exchange network 117. Each software driver 108, 110, 112, 114 and 116, in turn has a hardware interface 118, 120, 122, 124 or 126, respectively, associated therewith, and each hardware interface 118, 120, 122, 124 and 126 is connected to a respective transmission link 128, 130, 132, 134 or 136, such as an optical link, to the respective systems or central work station 6. A software driver 140 is associated with a hardware interface 142, disposed at the central work station 6.

The optical links can be of a conventional type, such as light waveguides which are internationally referenced with the designation RS 232.

The implementation of the hardware interface at the central work station 6 is dependent on the type or computer system which is employed at the central work station 6. This hardware interface, for example, may be a known hardware interface of the type used to connect a personal computer (PC) to a network. The software driver at this location is matched to the corresponding operating system, for example, DOS-OS for personal computers.

Although modifications and changes may be suggested by those skilled in the art, it is the intention of the inventors to embody within the patent warranted hereon all changes and modifications as reasonably and properly come within the scope of their contribution to the art.

We claim as our invention:

1. A medical diagnostics installation comprising:
a plurality of different medical examination systems, each system having a plurality of components, a portion of each plurality of components having operating parameters associated therewith and a further portion of each plurality of components acquiring data from a patient;
a network interconnecting said plurality of different medical examination systems;
a central work station disposed at one location of said network and connected to all of said components in said pluralities of components, including means, at said one location, for displaying, acquiring and setting said operating parameters of all of said components in said pluralities of components; and
a patient-proximate control panel for separately controlling at least some of said components in said pluralities of components, said patient-proximate control panel including control elements for immediate control of operation of a least some of said pluralities of components.

* * * * *